(12) United States Patent
Nishikawa et al.

(10) Patent No.: US 6,975,227 B1
(45) Date of Patent: *Dec. 13, 2005

(54) METHOD FOR CONTROLLING COMING AND GOING PERSONNEL, AND A SYSTEM THEREOF

(75) Inventors: Yoshihiro Nishikawa, Hitachi (JP); Sakae Gotou, Hitachioota (JP); Yasunobu Fujita, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 58 days.

This patent is subject to a terminal disclaimer.

(21) Appl. No.: 10/622,483

(22) Filed: Jul. 21, 2003

Related U.S. Application Data

(63) Continuation of application No. 09/908,841, filed on Jul. 20, 2001, now Pat. No. 6,621,414.

(30) Foreign Application Priority Data

Aug. 24, 2000 (JP) .............................. 2000-259381

(51) Int. Cl.⁷ ............................................. G08B 13/00
(52) U.S. Cl. .................... 340/541; 340/540; 340/545.2
(58) Field of Search ................................ 340/506, 517, 340/521, 522, 527, 540, 541, 545.2, 550; 250/281, 282, 324; 435/6, 91.1

(56) References Cited

U.S. PATENT DOCUMENTS

| | | |
|---|---|---|
| 3,645,127 A * | 2/1972 | Mongodin et al. ............ 73/40.7 |
| 4,060,039 A | 11/1977 | Lagarrigue |
| 4,586,441 A | 5/1986 | Zekich |
| 4,820,920 A | 4/1989 | Bather |
| 5,202,561 A | 4/1993 | Giessmann et al. |
| 5,479,012 A | 12/1995 | Wells |
| 6,621,414 B2 * | 9/2003 | Nishikawa et al. .......... 340/541 |
| 6,686,592 B1 * | 2/2004 | Sakairi et al. ............... 250/324 |

FOREIGN PATENT DOCUMENTS

| | | |
|---|---|---|
| EP | 0 458 622 A2 | 11/1991 |
| JP | 11-352032 | 12/1999 |
| WO | WO 00/23958 | 4/2000 |

* cited by examiner

*Primary Examiner*—Van T. Trieu
(74) *Attorney, Agent, or Firm*—Dickstein Shapiro Morin & Oshinsky LLP

(57) ABSTRACT

A coming and going personnel control system having a high security level by prohibiting a coming person who has dealt with a dangerous substance from entering a facility through a control area is disclosed. Whether a person coming into the control area carries a dangerous substance such as explosive material with him or has dealt with such dangerous substance can be checked by the steps of: ionizing air which has been contacted with the person coming into a control area by a discharging device; the ionized air is detected by a mass spectrometer as a molecular weight; the molecular weight is input into a control processor; and if the detected molecular weight is matched with a molecular weight of dangerous substance which have been registered previously into the control processor, the door in a direction forward to the coming person is closed.

8 Claims, 8 Drawing Sheets

METHOD FOR CONTROLLING COMING AND GOING PERSONNEL, AND A SYSTEM THEREOF

This application is a continuation of application Ser. No. 09/908,841 filed on Jul. 20, 2001, now U.S. Pat. No. 6,621,414, which claims priority under 35 U.S.C. 119 to the following foreign application: Japanese Application No. 2000-259381, dated Aug. 24, 2000, the disclosure of both of which are hereby incorporated by reference.

BACKGROUND OF THE INVENTION

The present invention relates to a system for controlling coming and going personnel at an important facility such as a nuclear power plant and the like.

A conventional gate for controlling the coming and going personnel is operated only for checking whether a person is qualified to enter a control area or not. For instance, in order to check the qualification of a coming person, various personal information are stored in the system; the coming person makes the system read his ID card and the like in order to make the system identify his personal information; and the system judges whether the person is qualified to enter the control area or not by retrieving his personal information based on the input from his ID card and the like.

The gate for controlling the coming and going personnel is at least provided with a card reader for reading the ID card and a gate to control passage of the coming and going personnel. Whether the coming person carries a dangerous substance with him or not is checked by a metal detector and the like used in air ports and other various places other than the gate for controlling the coming and going personnel, and the passage of the coming person is manually controlled. An example of prior art of a facility to control the coming and going personnel is disclosed in JP-A-11-352032 (1999).

In accordance with the prior art, only a metallic product is detected as a dangerous substance. If the control area is a power station, for instance, metallic tools and the like are brought in frequently, and the coming person has to bring in the tools through another gate than a gate for controlling the coming person. Moreover, because only a metallic product is detected, the prior art is not effective when dangerous explosives are brought in. Accordingly, a gate for controlling the coming and going personnel, which can readily detect dangerous explosives in addition to control coming and going personnel, is required.

SUMMARY OF THE INVENTION

One of the objects of the present invention is to provide a system for controlling coming and going personnel at a facility, in order to distinguish a coming person who dealt with dangerous substance and to prevent the facility from causing a hazardous accident previously.

In order to achieve the above object, the system for controlling coming and going personnel of the present invention comprises the steps of:

ionizing air, which has contacted with a coming person in a control area, by a discharging device, detecting the ionized air by a mass spectrometer as a molecular weight, and shutting a door in a direction forward the coming person, when the molecular weight is detected as the molecular weight of a dangerous substance which has been registered in a control processor, by a door driving controller which received a detected signal of the dangerous substance, so as to prohibit the coming person, who dealt with the dangerous substance, from entering the facility.

DESCRIPTION OF THE PREFERRED EMBODIMENTS

Figure 1:
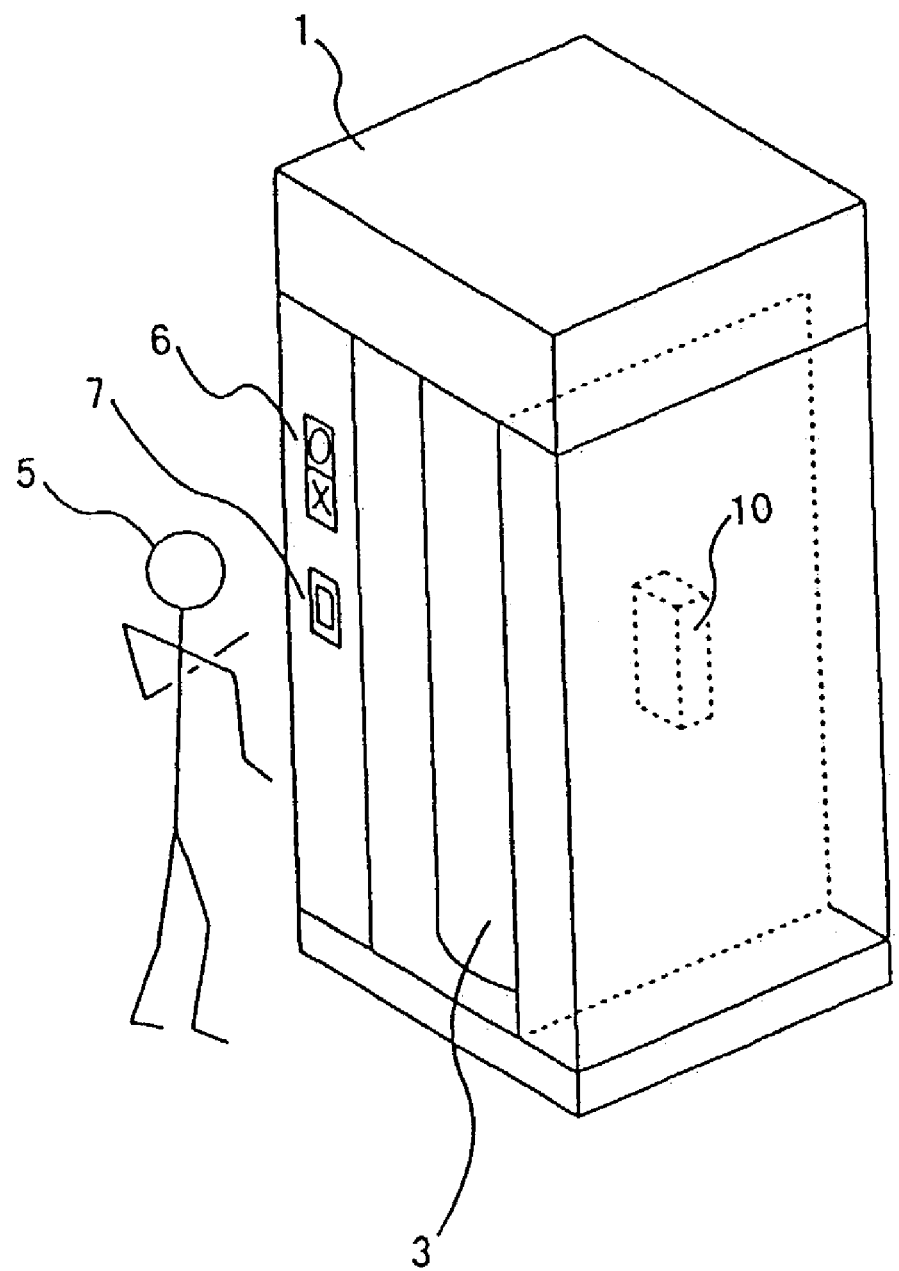
FIG. 1 is a schema tic perspective view of a coming and going personnel control gate indicated as an embodiment of the present invention.
Figure 2:
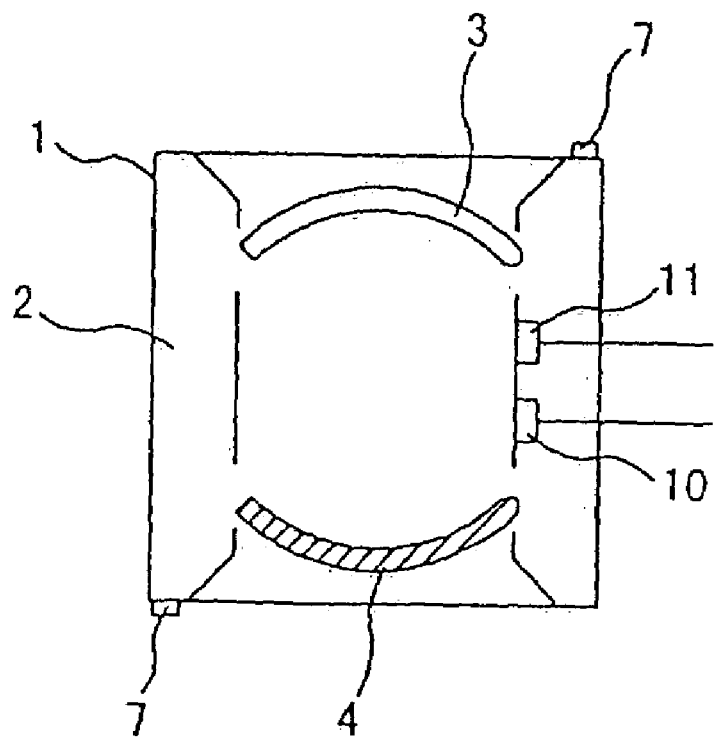
FIG. 2 is a schematic horizontal cross-sectional view of the coming and going personnel control gate shown in FIG. 1.
Figure 3:
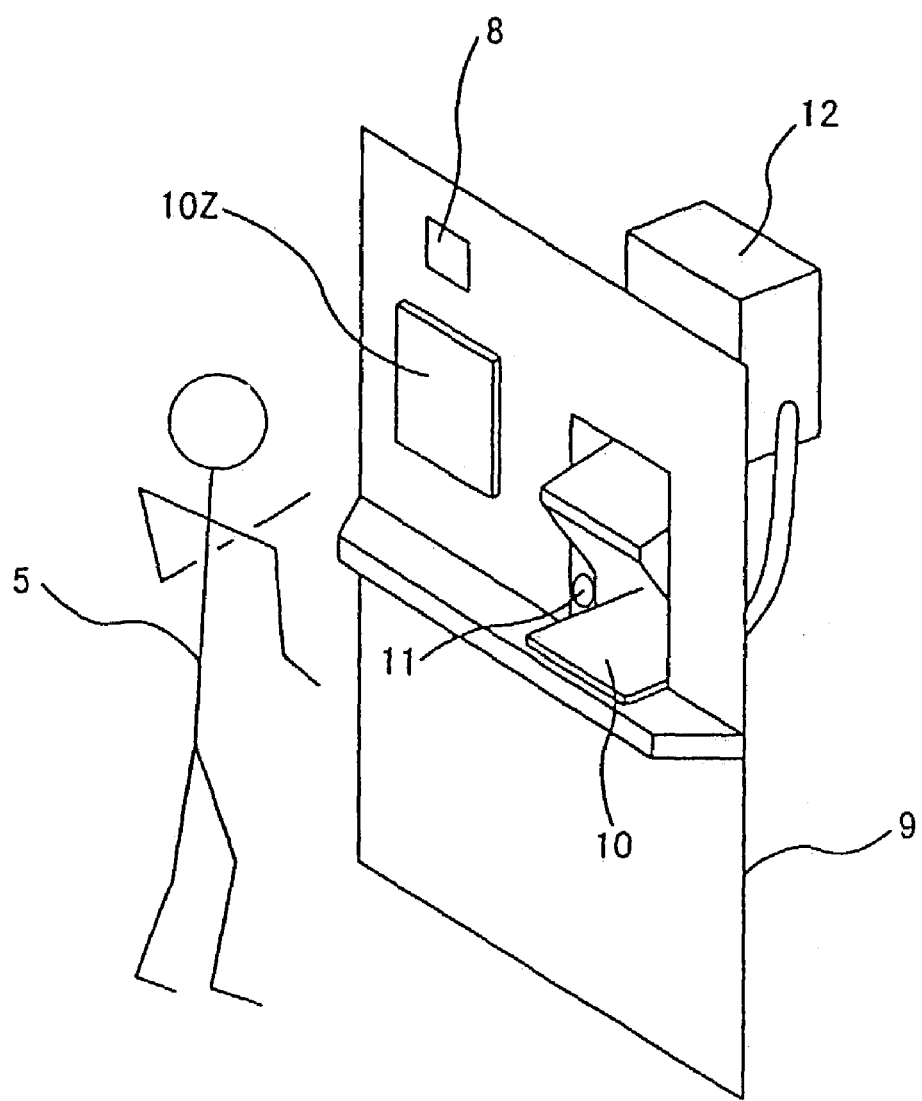
FIG. 3 is a schematic perspective view of a panel plate indicating an interior of the coming and going personnel control gate shown in FIG. 1 and FIG. 2.

FIG. 1 indicates a coming and going personnel control gate, of which cross section is indicated in FIG. 2. FIG. 3 indicates an interior of the coming and going personnel control gate partially, and FIG. 4 and FIG. 5 indicate a part of the palm shape detector.

Figure 6:
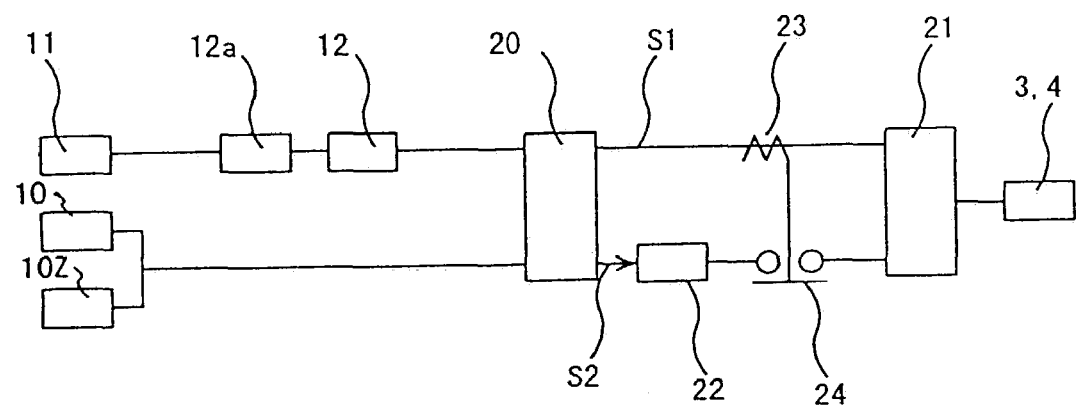
FIG. 6 is a block diagram of control processing for explaining control of processing route of the equipment shown in FIG. 2 to FIG. 5.

The coming and going personnel control gate 1 shown in FIG. 1 is provided with a control area 2 between outside and inside of the facility. The control area has an entrance door 3 and the exit door 4 between outside and inside of the control area. These doors are operated by the door driving controller 21 shown in FIG. 6.

Figure 9:
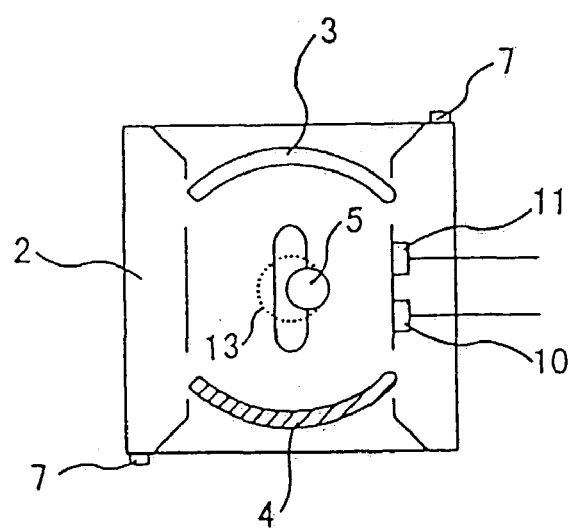
FIG. 9 is a cross sectional view of the coming and going personnel control gate for explaining the steps of making a person enter a control area from outside, and making the person go out from the control area through the equipment shown in FIG. 1 to FIG. 6.

As shown in FIG. 1 and FIG. 2, the entrance door 3 controls the coming person 5 who passes through the gate, and an exit door 4 is provided at a side opposite to the entrance door. When a coming person 5 wants to enter the control area, the coming person judges first whether the coming and going personnel control gate is capable of operation or not by watching a display lamp 6. If the coming and going personnel control gate is operable, the coming person enters inside of the coming and going personnel control gate, i.e. the control area 2, by pushing an area-entering button 7. After the coming person entered the control area 2, the entrance door 4 is closed, and the coming person is enclosed in the control area of the coming and going personnel control gate. A path panel 9 shown in FIG. 9 is provided in the control area, and the coming person 5 let a card reader 10z read his ID card first.

The coming and going personnel control system displays a guidance to put a hand onto the palm shape detector 10 on a display apparatus 8 after reading the ID card, i.e. a personal identification means. When the coming person 5 puts his hand onto the palm shape detector 10, air in the vicinity of hand of the coming person 5 is sucked by a suction pipe 11 and sent to a mass spectrometer 12. The guidance td put hand onto the palm shape detector 10 may also be displayed on the display apparatus 8 at a time when the coming person 5 enters the control area 2.

Figure 4:
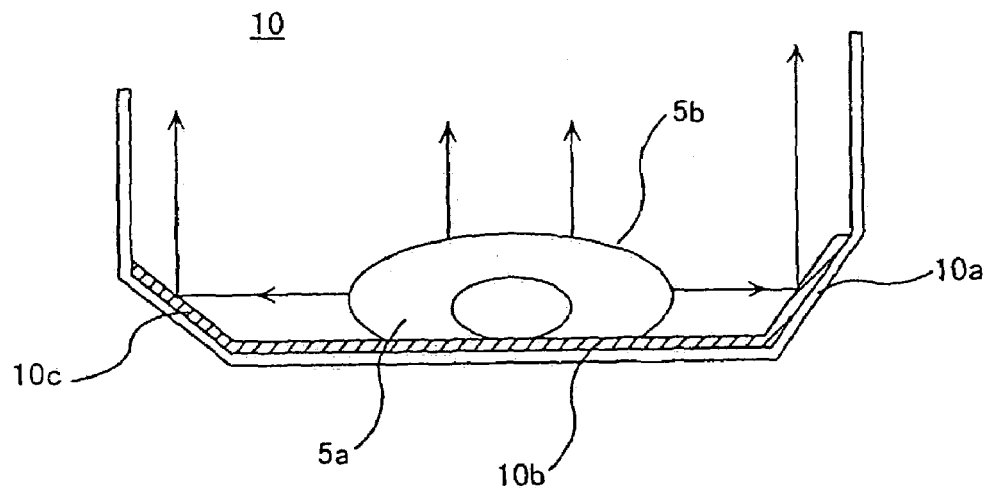
FIG. 4 is a partial cross sectional view of the palm shape detector shown in FIG. 3.
Figure 5:
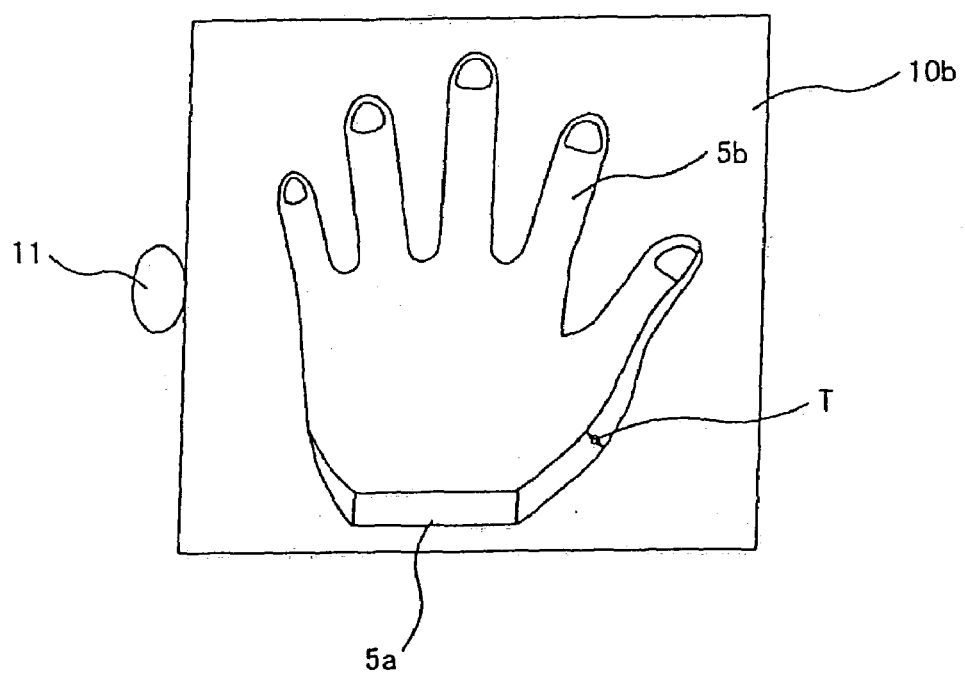
FIG. 5 is a plan view of the palm shape detector shown in FIG. 4 looking downward.

The palm shape detector 10 comprises a reflecting mirror 10b supported on a supporter 10a as shown in FIG. 4 and FIG. 5, and inclined mirrors 10c supported on inclined supporters at both left and right sides of the reflecting mirror 10b. When the hand 5a of the coming person 5 is placed on the reflecting mirror 10b, the palm shape 5b of the coming person 5 and a thickness T of the hand of the coming person are detected by the reflecting mirror 10 and the inclined mirrors 10c from a direction indicated by arrows, and input into the control processor 20 shown in FIG. 6 as plural personal palm shape data by a digital camera (CCD) provided at an upper portion of the mirrors. In accordance with the ID number read from the ID card 10z, the palm shape data of the coming person is retrieved from plural personal palm shape data which have been previously stored in the control processor 20. Although both ID card and the palm shape data can be used, a case only the palm shape data are used is explained in the following embodiment.

The air contacted with the coming person 5 is sucked into a corona discharging device 12a of the mass spectrometer, the air is ionized by the corona discharging device 12a, and molecular weight of the air is detected by the mass spectrometer. The molecular weight is input into the control processor 20'. Palm shape data of coming personnel who pass through the control area routinely are registered previously in the control processor 20. Further, molecular weight of dangerous substances, for instance, explosives, drugs, and the like are registered in the control processor 20.

Then, steps of passing through the control area 2 into the facility of the coming person 5 who entered the control area from outside are explained hereinafter referring to FIG. 6 to FIG. 10.

Figure 7:
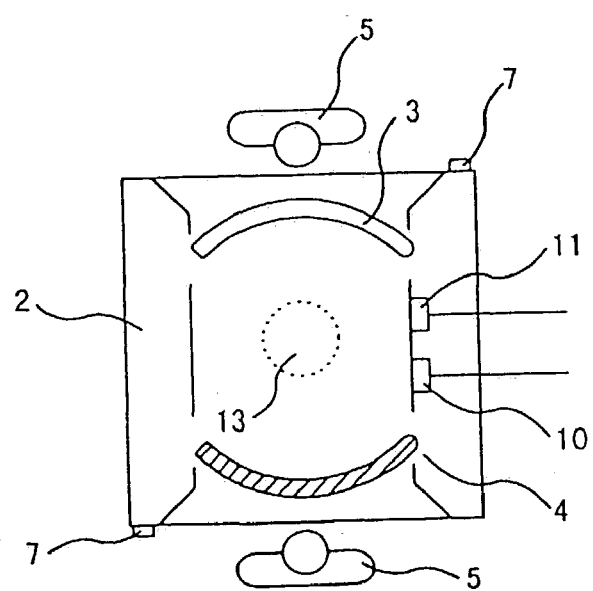
FIG. 7 is a cross sectional view of the coming and going personnel control gate for explaining the steps of making a person enter a control area from outside, and making the person go out from the control area through the equipment shown in FIG. 1 to FIG. 6.
Figure 8:
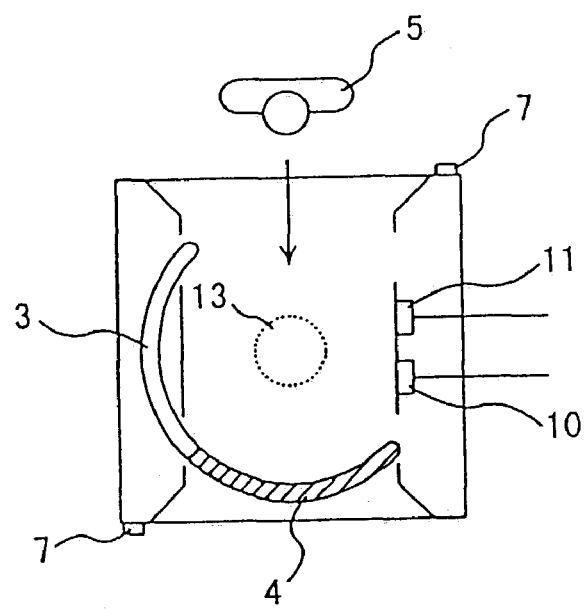
FIG. 8 is a cross sectional view of the coming and going personnel control gate for explaining the steps of making a person enter a control area from outside, and making the person go out from the control area through the equipment shown in FIG. 1 to FIG. 6.

The entrance door 3 and the exit door 4 are in a closed condition as shown in FIG. 7. Under this condition, the coming person 5 looks at the display lamp 6 shown in FIG. 1 and judges whether the control gate is operable or not. If it is judged as operable, the coming person pushes the area-entering button 7. Then, the entrance door 3 is opened as shown in FIG. 8, and the coming person 5 enters the control area 2 as shown in FIG. 9. An in-area switch 13 is provided under floor of the control area as shown in FIG. 9, and when the in-area switch 13 is turned to ON, the entrance door 3 is closed.

Under the condition shown in FIG. 9, the coming person 5 puts his hand 5a onto the palm shape detector 10. The palm shape 5b and a thickness T of the hand 5a of the coming person 5 are detected by the reflecting mirror 10a and the inclined mirrors 10b from a direction indicated by arrows, and the personal palm shape detected by a digital camera (CCD) provided at above the mirrors is input into the control processor 20 shown in FIG. 6 as plural personal palm shape data.

The air in the vicinity of hand 5a of the coming person 5 is sucked by the suction pipe 11, introduced into the discharging device 12a for ionizing, then, introduced into the mass spectrometer 12 for detecting as a molecular weight, and the molecular weight is input in the control processor 20.

Figure 10:
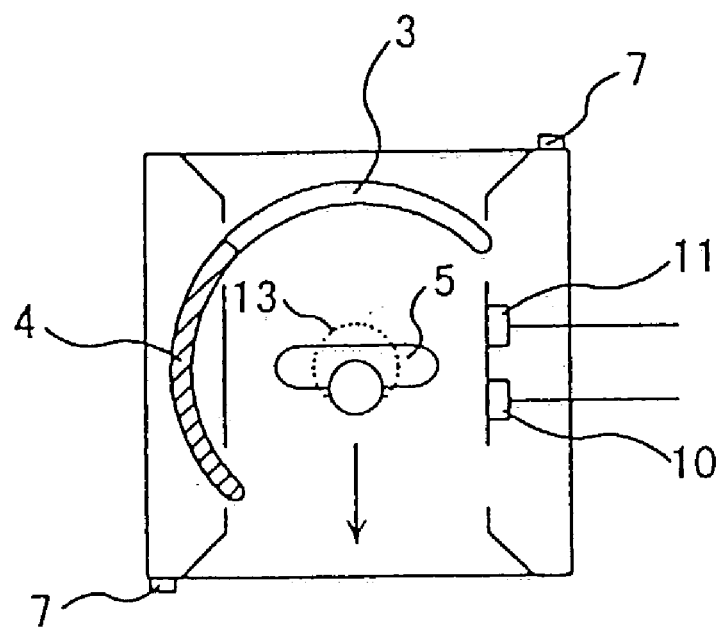
FIG. 10 is a cross sectional view of the coming and going personnel control gate for explaining the steps of making a person enter a control area from outside, and making the person go out from the control area through the equipment shown in FIG. 1 to FIG. 6.

The data on the palm shape and the molecular weight input in the control processor 20 are compared with the palm shape data and molecular weight data of dangerous substances, which are previously registered in the control processor. As a result of comparison, if the molecular weight is not matched with any molecular weight of dangerous substances and the detected palm shape is matched with one of previously registered palm shape data, the exit door 4 is opened as shown in FIG. 10. Then, the coming person 5 enters the facility from the control area 2, and the exit door 4 is closed as shown in FIG. 7 by turning off the in-area switch 13.

If a molecular weight of dangerous substances is detected by matching the detected molecular weight with one of molecular weights of dangerous substances which are previously registered in the control processor 20, the exit door 4 in the direction of forward the coming person 5 is closed by instructing the door driving apparatus 21, even if the detected palm shape is matched with one of previously registered palm shape data. The instruction to close the exit door 4 is given a priority to the instruction to open the exit door 4.

When a danger signal S1 on the dangerous substance and a palm shape signal S2 on the palm shape data are transmitted from the control processor 20 simultaneously, the palm shape signal S2 is input into a delay circuit 22. Therefore, the danger signal S1 reaches the door driving apparatus 21 faster than the palm shape signal S2, and a palm shape side switch 24 at the palm shape data side is made open by detecting a current of the danger signal S1 by a current detector 23. The palm shape side switch 24 is made close when flow of the danger signal S1 is stopped.

As the result, because the exit door 4 is closed by the door driving apparatus 21 and the coming person who dealt with dangerous substances can be prevented from entering the facility, the coming person 5 who dealt with dangerous substances can be identified, and causing a hazardous accident can be prevented previously.

Because the suction pipe 11 is provided adjacent to the palm shape detector 10, only the air in the vicinity of hand of the coming person is sucked. Accordingly, an amount of air to be sucked can be smaller in comparison with a case when all the air in the control area is sucked, and time for detecting molecular weight by the mass spectrometer and processing time for comparing molecular weight by the control processor 201 can be reduced. Furthermore, an advantage that small scale mass spectrometer 12 is sufficient for the detection can be achieved. Particularly, chemical substances contained in explosives such as nitroglycerine and the like have a property that the substances are remained on hands of the person who dealt with, and it is not easy to remove the substance from the place where it remains. Therefore, sucking the air only in the vicinity of the hand of the coming person is effective for detecting dangerous substances.

The coming and going personnel control system can be simplified by sucking the air only in the vicinity of the hand of the coming person 5 by the palm shape detector 10, because the control area is only required to be provided with doors between guides which guides the coming person, and the guide is only required to be provided with the palm shape detector 10 and the air suction inlet. Furthermore, because palm is utilized for identification and display means, the coming person can enter the control area even if the person forgets to carry an ID card with him.

Even if a palm shape signal S2 is faster than a danger signal S1, the danger signal S1 can be made reach the door driving controller 21 faster than the palm shape signal by adjusting with a delay circuit 22. However, if the danger signal S1 is not transmitted while adjusting with the delay circuit 22, an open instruction to the exit door 4 is instructed by the palm shape signal S2.

When a person in the facility goes out through the control area, the steps reverse to the above mentioned steps may be taken. A large number of personnel are coming for work, or going out by finishing work, the entrance door and the exit door are kept open, and only a last door in a direction of forwarding the personnel is closed. A place where a large number of indefinite personnel, who have no identification display means, are coming and going, a mass spectrometer for detecting dangerous substance must be provided. The identification display means includes a passing allowance cards, such as ticket, entrance ticket, and the like. The palm shape detector may measure the palm shape and thickness t of hand of the coming person by conventional methods such as electromagnetic method, ultrasonic method, and the like.

In the present embodiment, the delay circuit and the palm shape switch are provided in order to facilitate the explanation. However, the delay circuit and the palm shape switch can be omitted, because the functions of the delay circuit and the palm shape switch can be replaced with processing by a software of the control processor. The control processor is processed with a software which has the same function as the delay circuit and the palm shape switch. In a case when only a delay circuit is provided, a detection accuracy can be further improved by providing a detector for detecting danger signal to the delay circuit.

Figure 11:
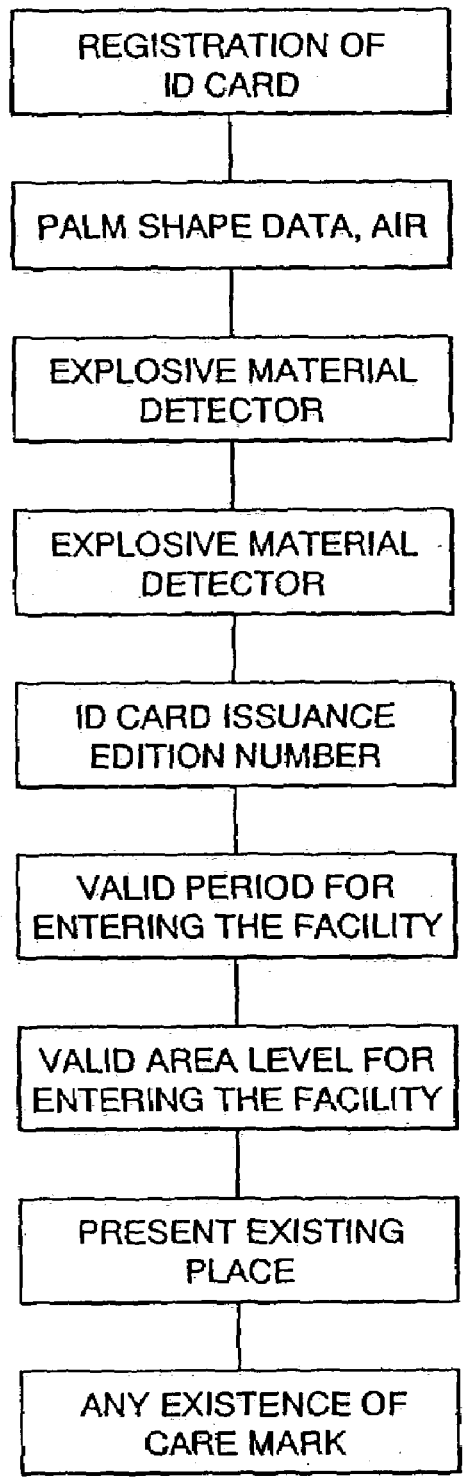
FIG. 11 is a flow chart for explaining an example of checking methods using an ID card and a palm shape data with the coming and going personnel control system.

Then, in accordance with the system for controlling coming and going personnel, an example of checking method using an ID card and palm shape data is explained hereinafter referring to FIG. 11. First, the personal information which are previously stored in the system are retrieved depending on the ID number written on the ID card. When the personal information is previously registered, the palm shape data read by the palm shape detector is checked first whether the detected palm shape data are matched with the previously registered palm shape data. In a case when the detected palm shape data are matched with the previously registered palm shape data, a check whether the person is authorized for entering the control area or not is performed. At first of the authorization check, confirmation that no detection of any molecular weights of dangerous substances is performed.

The theory of the dangerous substance check is as follows: First, the substance contained in the sucked air is ionized by corona discharging in the air; the molecular weight of the ionized substance is determined by a mass spectrometer; the determined molecular weight is compared with molecular weights of dangerous substances which are previously registered in order to confirm no molecular weight of dangerous substance is contained.

If any dangerous substance is contained, an alarm is sounded; the coming person is enclosed in the control area by closing and locking all the door; or the door forward the coming person is closed. If no dangerous substance is contained, personal information of the coming person is checked. The check is performed on the personal information, for instance, such as ID card issuance edition number, valid period for entering the facility, valid area level for entering the facility, present existing place, any existence of care marks, and others.

The ID card issuance edition number is used for checking whether the number of issuance is correct even if the card is re-issued by lost of the card, in order to confirm that the ID card is not the lost one.

The valid period for entering the facility is used for checking whether the coming into the facility is performed during an allowed period.

The valid area level for entering the facility is used for checking whether the coming person is authorized with a level to enter the facility where the coming person wants to enter.

The present existing place is used for checking whether the existing place of the card holder which is being tracked by the system is matched with the place of the coming and going personnel control gate, in order to prevent improper use of the card such as double issuance of the card.

The care mark has a function to set temporary prohibition by the issuer to use a lost ID card and others, and the care mark is used for checking whether such prohibition has been set or not.

After checking a series of the above various items, if no problem is found, the coming person is allowed to enter the facility by opening the forward door.

The checking system is installed in a manner that air in the vicinity of hand placing portion of the palm shape detector, which is provided in order to perform personal identification of the coming person, can be sucked, and the sucked air is introduced into a mass spectrometer. That is, the chemical substances, which are contained in explosive materials, such as nitroglycerine and the like have such a property that they are adhered to hands even after they have been handled, and they are not easily removed from the hands. Therefore, for instance, in an airport, dangerous substances can be traced with passports by utilizing the above property. Accordingly, a system for controlling coming and going personnel having a significantly high security level can be constructed by sucking air in the vicinity of the palm shape detector which is installed in the coming and going personnel control gate, and analyzing by a mass spectrometer, because tracing of explosive substances can be performed readily.

If a course of action of the coming person is restricted in the control area of the gate in order to detect dangerous substances in a condition that the coming person is in the control area of the coming and going personnel control gate, an advantage that the detection of dangerous substances and prohibition of coming into the facility can be achieved remotely.

Furthermore, because the air to be sucked is restricted to only air in the vicinity of the palm shape detector, the size of the sucking apparatus can be reduced.

In accordance with the present invention described above, an accident caused by explosive substances can be prevented previously by checking automatically whether a coming person into the facility is related to the dangerous substance or not, or whether the person intends to bring explosive substances into the facility.

What is claimed is:

1. A method for controlling coming and going personnel at a facility comprising the steps of:
   ionizing air by a discharging device, the air has been contacted with a coming person who entered into a control area provided between outside and inside of the facility;
   detecting the ionized air by a mass spectrometer as a molecular weight;
   inputting the molecular weight into a control processor;
   checking the molecular weight against molecular weights of dangerous substance which have been registered previously into said control processor to detect the molecular weight of dangerous substance in the air;
   inputting a signal of the detected dangerous substance into a door driving controller; and
   closing a door provided in the control area by operating said door driving controller to prohibit said coming person from entering the facility.

2. A system for controlling coming and going personnel at a facility comprising:
   a control area provided between outside and inside of the facility;
   doors provided in said control area;
   a door driving controller for controlling operation of said doors; and
   a mass spectrometer provided in said control area for ionizing air by a discharging device, the air been contracted with a coming person who entered into said control area, and detecting the ionized air as a molecular weight; wherein
   said molecular weight is input into a control processor to check against molecular weights of dangerous substance, which have been registered previously into said control processor, in order to detect the molecular weight of dangerous substance in the air;
   a signal of the detected dangerous substance in the air is input into a door driving controller; and
   the door provided in a direction forward of the coming person is closed by operating said door driving controller.

3. A system for controlling coming and going personnel at a facility comprising:
   a control area provided between outside and inside of the facility;
   doors provided in said control area;
   a door driving controller for controlling operation of said doors;
   a person identification detector provided in said control area for identifying a personal identification means of a coming person; and
   a mass spectrometer provided in said control area for ionizing air by a discharging device, the air has been contacted with a coming person who entered into said control area, and detecting the ionized air as molecular weight; wherein
   said detected personal identification and said detected molecular weight are input into a control processor to check against personal identification and molecular weights of dangerous substance, both of which have been registered previously into said control processor, in order to detect the molecular weight of dangerous substance in the air and the personal identification matching with the previously registered personal identification;
   a danger signal of the detected dangerous substance in the air and an identification signal of the detected personal identification matching with the previously registered personal identification are input into said door driving controller, respectively;
   said danger signal is input into said door driving controller prior to said identification signal, of which transmission is delayed by a delay element provided in said identification signal side; and
   the door provided in a direction forward of the coming person is closed by operating said door driving controller.

4. A system for controlling coming and going personnel at a facility comprising:
   a controller area provided between outside and inside of the facility;
   doors provided in said control area;
   a doors driving controller for controlling operation of said doors;
   a palm shape detector provided in said control area for detecting a palm shape of a coming person; and
   a mass spectrometer provided in said control area for ionizing air by a discharging device, the air has been contacted with said palm shape, and detecting the ionized air as a molecular weight; wherein
   said palm shape and said detected molecular weight are input into a control processor to check against palm shapes and molecular weights of dangerous substances, both of which have been registered previously into said control processor, in order to detect the molecular weight of dangerous substance in the air and the palm shape matching with the previously registered palm shapes;
   a danger signal of the detected dangerous substance in the air and a palm shape signal of the detected palm shape matching with the previously registered palm shapes are input into said door driving controller, respectively;
   said danger signal is input into said door driving controller prior to said palm shape signal, of which transmission is delayed by a delay element provided in said palm shape signal side; and
   the door provided in a direction forward of the coming person is closed by operating said door driving controller.

5. A method for controlling coming and going personnel at a facility comprising:
   identifying a personal identification of a coming person by a person identification detector provided in a control area between outside and inside of the facility;
   ionizing air by a discharging device and detecting the ionized air as a molecular weight by a mass spectrometer provided in the control area;
   inputting the detected personal identification and the detected molecular weight into a control processor to check against personal identification and molecular weights of dangerous substance, both of which have been registered previously into the control processor, in order to detect the molecular weight of dangerous substance in the air and the personal identification matching with the previously registered personal identification; and
   generating a danger signal when a dangerous substance is detected in the air and generating an identification signal when the detected personal identification is matched with the previously registered personal identification, and allowing the coming person to enter into the facility when no danger signal exists and an identification signal exists.

6. A method for controlling coming and going personnel at a facility comprising:
- identifying a person identification in a control area between outside and inside of the facility by detecting the hand of a coming person; and
- ionizing air by a discharging device and detecting the ionized air as a molecular weight by a mass spectrometer provided in the control area, the mass spectrometer detecting the air in the vicinity of the hand of the coming person who entered into said control area;
- inputting the detected personal identification and the detected molecular weight into a control processor to check against personal identification and molecular weights of dangerous substance, both of which have been registered previously into said control processor, in order to detect the molecular weight of dangerous substance in the air and the personal identification matching with the previously registered personal identification; and
- generating a danger signal when a dangerous substance is detected in the air and generating an identification signal when the detected personal identification is matched with the previously registered personal identification and allowing the coming person to enter into the facility when no danger signal exists and identification signal exists.

7. A method for controlling coming and going personnel at a facility comprising:
- identifying a personal identification of a coming person by a person identification detector provided in a control area provided between outside and inside of the facility;
- ionizing air by a discharging device and detecting the ionized air as a molecular weight by a mass spectrometer provided in the control area, the mass spectrometer detecting the air in the vicinity of hand of the coming person who entered into the control area;
- inputting the detected personal identification and the detected molecular weight into a control processor to check against personal identification and molecular weights of dangerous substance, both of which have been registered previously into the control processor, in order to detect the molecular weight of dangerous substance in the air and the personal identification matching with the previously registered personal identification;
- generating a danger signal when a dangerous substance is detected in the air and generating an identification signal when the detected personal identification is match with the previously registered personal identification are input into a door driving controller for controlling operation of an entrance door and an exit door provided in the control area, respectively;
- inputting the danger signal into the door driving controller prior to the identification signal, of which transmission is delayed by a delay element provided in the identification signal side; and
- closing the exit door provided in a direction forward of the coming person by operating the door driving controller.

8. A method for controlling coming and going personnel at a facility comprising:
- detecting a palm shape of a coming person with a palm shape detector provided in the control area;
- ionizing air by a discharging device and detecting the ionized air as a molecular weight by a mass spectrometer provided in a control area provided between outside and inside of the facility, the mass spectrometer detecting the air in the vicinity of hand of the coming person who entered into said control area;
- inputting said palm shape and said detected molecular weight into a control processor to check against palm shapes and molecular weights of dangerous substance, both of which have been registered previously into said control processor, in order to detect the molecular weight of dangerous substance in the air and the palm shape matching with the previously registered palm shapes;
- generating a danger signal when a dangerous substance detected in the air and generating a palm shape signal when the detected palm shape is matched with the previously registered palm shapes are input into a door driving controller for controlling operation of an entrance door and an exit door provided in said control area, respectively;
- inputting the danger signal into the door driving controller prior to said palm shape signal, of which transmission is delayed by a delay element provided in said palm shape signal side; and
- closing the door provided in a direction forward of the coming person by operating the door driving controller.

* * * * *